US009401042B2

(12) United States Patent
Rodenburg et al.

(10) Patent No.: US 9,401,042 B2
(45) Date of Patent: Jul. 26, 2016

(54) METHOD AND APPARATUS FOR IMAGING A THREE DIMENSIONAL TARGET OBJECT USING INCIDENT RADIATION

(75) Inventors: John Marius Rodenburg, Sheffield (GB); Andrew Maiden, Sheffield (GB); Martin Humphry, Sheffield (GB)

(73) Assignee: PHASE FOCUS LIMITED, Sheffield (GB)

( * ) Notice: Subject to any disclaimer, the term of this patent is extended or adjusted under 35 U.S.C. 154(b) by 491 days.

(21) Appl. No.: 13/825,576

(22) PCT Filed: Sep. 22, 2011

(86) PCT No.: PCT/GB2011/051786
§ 371 (c)(1),
(2), (4) Date: Mar. 22, 2013

(87) PCT Pub. No.: WO2012/038749
PCT Pub. Date: Mar. 29, 2012

(65) Prior Publication Data
US 2013/0181990 A1 Jul. 18, 2013

(30) Foreign Application Priority Data

Sep. 24, 2010 (GB) .................................. 1016088.5
Jul. 5, 2011 (GB) .................................. 1111423.8

(51) Int. Cl.
*G06T 15/50* (2011.01)
*A61B 6/02* (2006.01)
*G01N 21/47* (2006.01)
*G01T 1/164* (2006.01)

(52) U.S. Cl.
CPC ................ *G06T 15/50* (2013.01); *A61B 6/027* (2013.01); *G01N 21/4795* (2013.01); *G01T 1/1647* (2013.01)

(58) Field of Classification Search
None
See application file for complete search history.

(56) References Cited

U.S. PATENT DOCUMENTS 6,483,891 B1 11/2002 Lazarev et al.
2010/0241396 A1* 9/2010 Rodenburg ................... 702/167

FOREIGN PATENT DOCUMENTS

| CN | 1985188 | 12/1934 |
| CN | 101820817 A | 9/2010 |
| JP | H11-339050 A | 12/1999 |

(Continued)

OTHER PUBLICATIONS

Rodenburg, J. M., A. C. Hurst, and A. G. Cullis. "Transmission microscopy without lenses for objects of unlimited size." Ultramicroscopy 107.2 (2007): 227-231.*

(Continued)

*Primary Examiner* — Mark Zimmerman
*Assistant Examiner* — Vu Nguyen
(74) *Attorney, Agent, or Firm* — Lando & Anastasi, LLP

(57) ABSTRACT

A method of providing image data for constructing an image of a region of a three dimensional target object, comprising providing, from a radiation source, incident radiation directed at a target object, detecting an intensity of radiation scattered by the target object, and determining image data for each of a respective plurality of slices within the target object each indicating one or more characteristics of the target object at a respective depth within the target object, wherein the image data is determined based on the detected intensity of radiation via an iterative process wherein running estimates of the image data for each of the plurality of slices are updated step by step.

29 Claims, 7 Drawing Sheets

(56) References Cited

FOREIGN PATENT DOCUMENTS

| JP | 2003-202305 A | 7/2003 |
| JP | 2010-528279 A | 8/2010 |
| WO | 2008/142360 A1 | 11/2008 |
| WO | 2010006405 A1 | 1/2010 |

OTHER PUBLICATIONS

International Preliminary Report on Patentability for International Application No. PCT/GB2011/051786, mailed Mar. 26, 2013, 8 pages.
International Search Report for International Application No. PCT/GB2011/051786 mailed Apr. 25, 2012, 5 pages.
Kirkland, Earl J., et al., "Image Simulation in Transmission Electron Microscopy", Jul. 26, 2006, pp. 1-14.
Liu, Cheng, et al., "Influence of Thick Crystal Effects on Ptychographic Image Reconstruction with Moveable Illumination", Ultramicroscopy 109, Jan. 29, 2009, pp. 1263-1275.
Maiden, Andrew M. et al, "Optical Ptychography: A Practical Implementation with Useful Resolution", Optics Letters, vol. 35, No. 15, Aug. 1, 2010, pp. 2585-2587.
Maiden, Andrew M. et al., "An Improved Ptychographical Phase Retrieval Algorithm for Diffractive Imaging", Ultramicroscopy, 109, Feb. 20, 2009, pp. 1256-1262.
Rosen, Joseph, "Computer-Generated Holograms of Images Reconstructed on Curved Surfaces", Applied Optics, vol. 38, No. 29, Oct. 10, 1999, pp. 6136-6140.

* cited by examiner

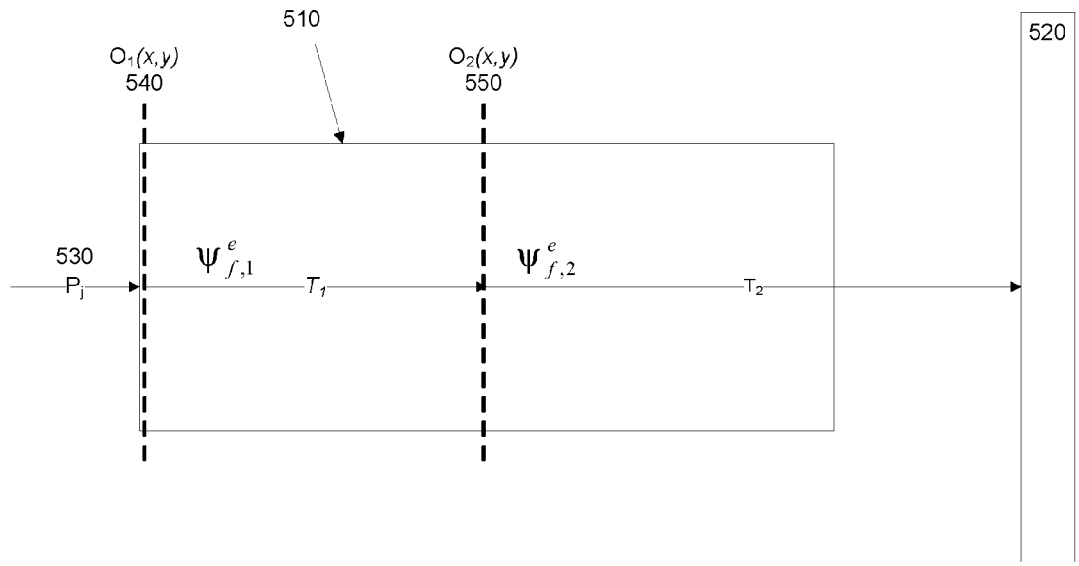
Fig. 5
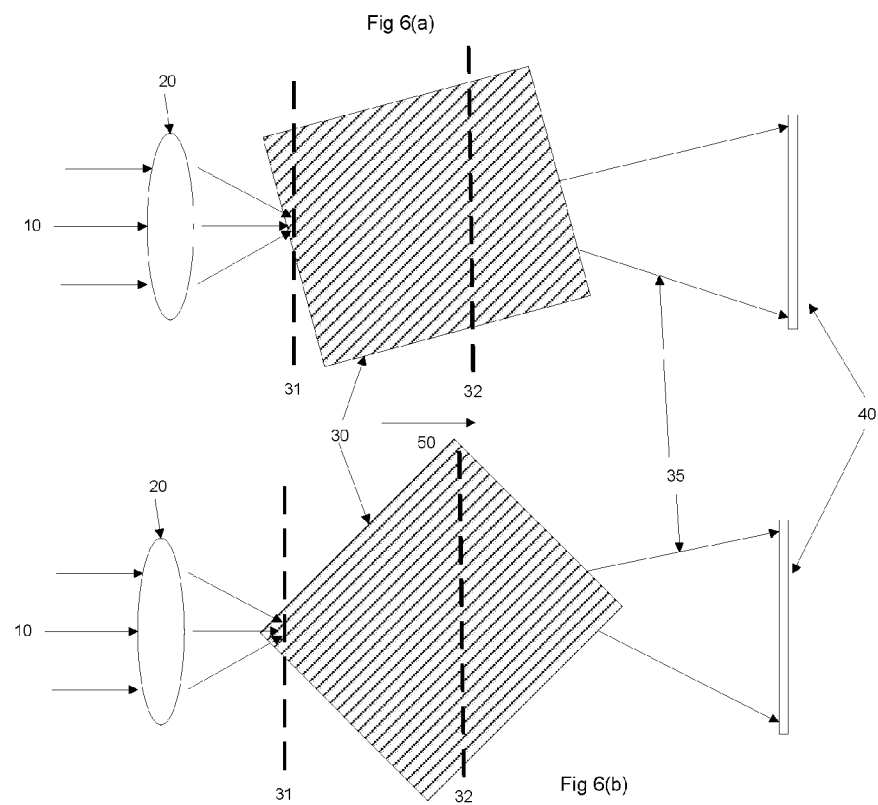

METHOD AND APPARATUS FOR IMAGING A THREE DIMENSIONAL TARGET OBJECT USING INCIDENT RADIATION

The present invention relates to a method and apparatus for providing image data from which an image of a target object may be generated. In particular, although not exclusively, embodiments of the present invention relate to methods and apparatus for obtaining image data from which three-dimensional images of a target object may be generated.

BACKGROUND

WO 2005/106531 by the present Applicant, which is herein incorporated by reference for all purposes, discloses a method for providing image data which may be used to construct an image of an object based on a measured intensity of several diffraction patterns. This method is known as a pytochgraphical iterative engine (PIE). In PIE an iterative phase-retrieval method is used to determine an estimate of the absorption and phase-change caused by the object to a wave field as it passes through or is reflected by the object. This method uses redundancy in the plurality of diffraction patterns to determine the estimate.

WO 2010/064051 by the present Applicant, which is incorporated herein by reference for all purposes, discloses an enhanced PIE (ePIE) method wherein it is not necessary to know or estimate a probe function. Instead a process is disclosed in which the probe function is iteratively calculated step by step with a running estimate of the probe function being utilised to determine running estimates of an object function associated with a target object.

WO 2008/142360 by the present Applicant, which is herein incorporated by reference, discloses a method of three dimensional imaging. In this method, a complex wave field of illumination is determined at a plurality of planes downstream of a source of the illumination. Typically, these planes intersect an object. Using knowledge of the illumination at each plane, an iterative process such as that disclosed in WO 2005/106531 or WO 2010/064051 may be performed to construct an estimate of the object at that plane, from which an image of the object at that plane may be produced. By repeating the iterative process for each of the plurality of planes, a three dimensional image of the object may be obtained.

However, problems have been noted in that images produced by the method of WO 2008/142360 may be complicated by Fresnel-type fringes relating to a plane adjacent to the plane of interest, such as a plane in front (upstream) or behind (downstream) of the plane of interest. Furthermore, the method takes no account of multiple scattering effects. That is to say, it does not take into account the effect of the object on the illumination as it propagates through the object, such as due to scattering from upstream layers of the object previously traversed by the illumination.

It is an object of embodiments of the invention to at least mitigate one or more of the problems of the prior art.

BRIEF DESCRIPTION OF THE DRAWINGS

Embodiments of the invention will now be described by way of example only, with reference to the accompanying figures, in which:

FIG. 5 an apparatus associated with the method of FIG. 4 according to an embodiment of the invention;

FIG. 6 shows an apparatus according to another embodiment of the invention;

DETAILED DESCRIPTION OF EMBODIMENTS OF THE INVENTION

In some embodiments of the invention illumination wave fields are determined at a plurality of slices. An estimate of the object is determined at each of the slices. An exit wave from each of the slices is determined as a result of interaction of the illumination with the object at that slice. The exit waves are propagated to a summation plane, which may or may not be a plane at which an estimate of the object is to be determined, wherein a composite wave is determined as a result of the contributions from the plurality of wave fields propagated to or determined at that plane (where the summation field is also a plane at which an exit wave is determined). The composite wave is propagated to a plane of a detector where an estimate of a diffraction pattern is determined. The estimated diffraction pattern is corrected based on a diffraction pattern measured by the detector before being reverse-propagated to each of the slices at which estimates of the object are to be determined. The estimates of the object are updated based on the reverse propagated wave. The method is performed iteratively wherein the plurality of estimates of the object are updated step-by-step with each iteration. In other words, the plurality of estimates is updated consecutively during each iteration of the method. Advantageously, this allows interactions between the various planes to be considered.

In other embodiments, an illumination wave field is determined at a first slice at which an estimate of the object is to be determined. An exit wave from that slice is determined and propagated to another slice at which an estimate of the object is to be determined. In other words, the propagated exit wave from a previous slice is utilised as an illumination wave field at a subsequent slice. An exit wave may be determined from the subsequent slice and the process repeated for all desired slices of interest. At a final slice the exit wave is propagated to a plane of a detector. After data recorded at the detector plane is used to adjust the modulus of the wave calculated at the detector, the wave is back-propagated to the exit or final slice of the object. The estimates of the object and the waves propagating within the object are updated based on the reverse propagated waves, in such a way that the sequential propagation involving multiple scattering is traced back through the object.

Figure 1:
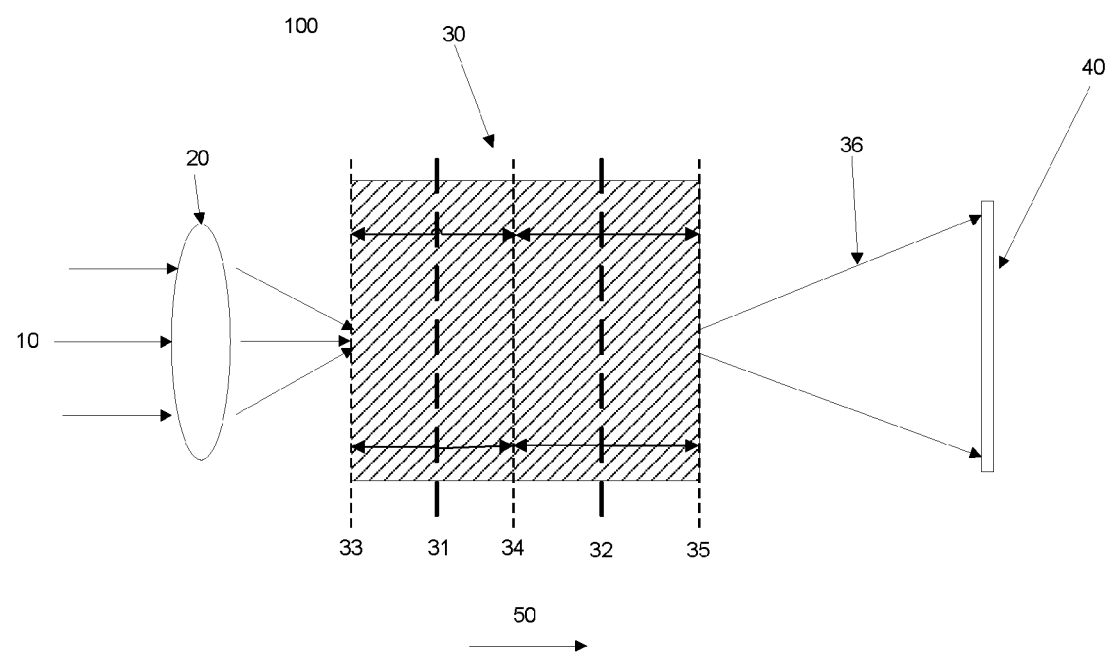
FIG. 1 shows an apparatus according to an embodiment of the invention.

FIG. 1 illustrates an apparatus 100 according to an embodiment of the invention. The apparatus 100 is suitable to provide three-dimensional image data of an object 30 which may, although not exclusively, be used to produce a three-dimensional image of at least a region of the object. By three-dimensional image data it is meant image data relating to a plurality of slices of the object 30, such as slices 31, 32 which intersect the object 30. Whilst two slices 31, 32 are shown it is envisaged that the image data may relate to more than two slices. In particular, the slices may be spaced apart along the direction of the optic axis 50. Whilst the slices 32, 32 are shown as planes, it will be understood that that the slices do not necessarily need to be planes i.e. to be flat. The slices 31, 32 may be otherwise shaped, such as curved.

A radiation source, which although not shown in FIG. 1, is a source of radiation 10 which falls upon a focusing arrangement 20, such as one or more lenses, and is caused to illuminate a region of a target object 30. Such illumination need not be formed by a lens, but could be produced by any sort of optical device, aperture or source, provided that the resulting wave that impinges upon the object is substantially localised and has within it an angular, but possibly arbitrary, distribution of incident beams.

It is to be understood that the term radiation is to be broadly construed. The term radiation includes various wave fronts. Radiation includes energy from a radiation source. This will include electromagnetic radiation including X-rays, emitted particles such as electrons. Other types of radiation include acoustic radiation, such as sound waves. Such radiation may be represented by a wavefront function $\psi(x,y)$. This wave function includes a real part and an imaginary part as will be understood by those skilled in the art. This may be represented by the wave function's modulus and phase. $\psi^*(x,y)$ is the complex conjugate of $\psi(x,y)$ and $\psi(x,y)\psi^*(x,y)=|\psi(x,y)|^2$, where $|\psi(x,y)|^2$ is an intensity which may be measured for the wave function.

The focussing arrangement or lens 20 forms a probe function $P(x,y)$ which is arranged to select a region of the target object 30 for investigation. $P(x,y)$ is the complex stationary value of this wave field calculated at a plane, such as slice 31. A respective probe function may be calculated for each of the plurality of slices 31, 32.

Incident radiation 10 thus falls upon the up-stream side of the target object 30 and is scattered by the target object 30 as it is transmitted. The target object 30 may be at least partially transparent to incident radiation. The target object 30 may or may not have some repetitive structure. Alternatively the target object 30 may be wholly or partially reflective in which case a scattering pattern is measured based on reflected radiation.

An exit wave $\psi(x,y)$ is thus formed after interaction of the radiation with the object 30, which can be approximated as a series of transmittance functions, as will be explained. In embodiments of the invention, a number of two-dimensional complex transmittance functions are utilised $O_n(x,y)$, where each corresponds to a slice within the object at a different distance $z_n$ along the optic axis 50, as illustrated for example 31 and 32 in FIG. 1.

In the case of approximating the object 30 as two slices, then it will be understood that a first slice 31 has an associated transmission function $O_1(x,y)$ which is related to an integral of the optical potential $V(x,y,z)$ in the z-direction between, for example, a plane 33 coincident with a front surface of the object 30 and a plane 34, for example, half way through $V(x,y,z)$ in the z-direction. It will be understood that the integral may also be determined between surfaces which are not flat, such as curved surfaces. A second slice 32 has an associated transmission function $O_2(x,y)$ which is similarly related to an integral in the z-direction of $V(x,y,z)$ from, for example, the plane 34 to, for example, a plane 35 coincident with the back (downstream) surface of the object 30. It will be understood that in approximating the object 30 as a series of slices 31, 32, the location of such slices 31, 32, and the range of z over which the integration is undertaken, can be chosen at will.

It can be assumed that, having formed $O_n(x,y)$, each such two-dimensional transmission function models the effect of changing the modulus and phase of an incident wave upon its front surface 33, 34, say $\psi^i(x,y)$, to give an exit wave, $\psi^e(x,y)$ at its rear surface 34, 35, via a simple multiplication, so that $\psi^e(x,y)=\psi^i(x,y)\cdot O_b(x,y)$.

The exit wave function $\psi^e(x,y)$ is an exit wave function of radiation as it exits a corresponding slice of the object 30, such as slice 31 or slice 32. This exit wave $\psi^e(x,y)$ may at least partly continue to propagate through the object 30 and may form a probe function for one or more downstream slices. Thus, for the first slice 31, it will be understood that $\psi^i(x,y)=P(x,y)$ and for the second slice 32, in some embodiments, $\psi_2^i(x,y)$ is $P(x,y)$ propagated to the second slice 32, or in some embodiments is the exit wave from the first slice 31, $\psi_1^e(x,y)$, propagated to the second slice, where the subscript indicates the appropriate slice. Eventually an exit wave from a last or final slice propagates 36 to a detector 40 to form a diffraction pattern $\Psi(u,v)$ at a diffraction plane, where u, v are two dimensional coordinates in the plane of the detector 40.

It will be understood that if the diffraction plane at which scattered radiation is detected is moved nearer to the specimen then Fresnel diffraction patterns will be detected rather than Fourier diffraction patterns, as discussed below. In such a case, the propagation function from the exit wave $\psi^e(x,y)$ to the diffraction pattern $\Psi(u,v)$ will be a Fresnel transform rather than a Fourier transform. It will also be understood that the propagation function from the exit wave $\psi^e(x,y)$ to the diffraction pattern $\Psi(u,v)$ may involve other physical arrangements which can be modelled using other transforms.

In order to select the region of the target object 30 to be illuminated or probed, the lens(es) 20 or aperture may be mounted upon an x/y translation stage which enables movement of the probe function with respect to the object 30. It will also be realised that the object 30 may be moved with respect to the lens(es) or aperture. The probe function 20 may be moved by the translation stage in an arrangement of positions.

The arrangement may be a grid which may comprise, for example, 20×20 positions, although other numbers of positions may be used and, furthermore, the grid may not comprise equal numbers of positions in both x and y directions. It is also envisaged that the arrangement may be circular or otherwise shaped and each position of the arrangement may include a respective offset.

The detector 40 is a suitable recording device such as a CCD camera or the like which allows the diffraction pattern to be recorded. The detector 40 allows the detection of the diffraction pattern in the diffraction plane. The detector 40 may comprise an array of detector elements, such as in a CCD.

Figure 2:
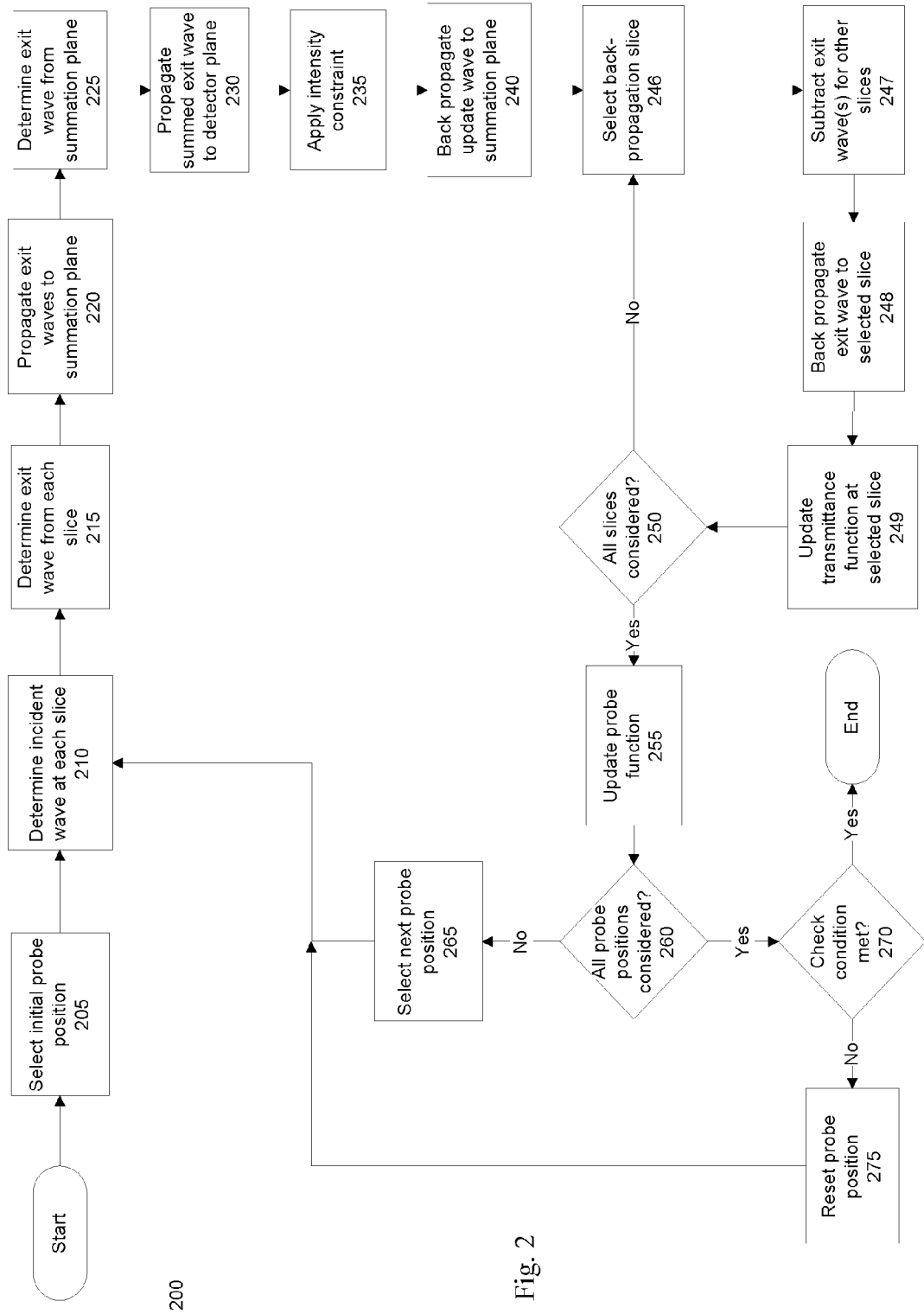
FIG. 2 shows a first method according to an embodiment of the invention.

A method 200 according to a first embodiment of the invention is shown in FIG. 2 and discussed with reference to FIG. 3. In this embodiment, running estimates of the exit wave from a plurality of slices are determined during each iteration of the method 200, i.e. are updated in a stepwise manner, and are combined at a plane before being propagated to a detector.

An object 30 of interest is decomposed into N slices n=1, 2,3 . . . N each lying at $z=z_n$ as shown in FIG. 3 for N=2 where a first slice is indicated with reference numeral 340 and a second slice as reference numeral 350. Each slice has an associated complex-valued transmission function of the form:

$$O_{n,actual}(x, y) = e^{i\sigma \int_{z_n}^{z_{n+1}} V(x,y,z)dz} \quad \text{Equation 1}$$

where σ is a scattering cross-section and the imaginary part of V(x,y,z) relates to the absorption of radiation by the object 30 and its real part relates to the phase change induced into a wave passing through the transmission function.

The separation of the slices 340, 350 in z i.e. along the optic axis need not be equal. The limits of the integration term may be from planes halfway between the previous and next slice, or over other ranges, as long as each voxel of the object 30 contributes to only one transmission function. In this example, the first slice 340 is coincident with a front surface of the object 310 for convenience of explanation, although it will be understand that this is not essential. The subscript 'actual' indicates that this transmission function is what we would obtain if we knew exactly the structure of the physical object 310.

In the following description $O_n(x,y)$ will represent a running estimate of the $n^{th}$ transmission function. Reconstruction algorithms according to embodiments of the invention are designed to iterate upon, i.e. to find, an accurate estimate of $O_n(x,y) \approx O_{n,actual}(x,y)$ for, at least some, or all N. In the case of electron scattering, V(x,y,z) may correspond to the atomic potential, or in the case of electromagnetic radiation, V(x,y,z) may correspond to the optical potential, as employed in the scalar theory of light scattering, or V(x,y,z) may correspond to some other property of the object 30 which, when integrated, gives rise to a similar transmission function as described by Equation 1, this also being true for some other types of radiation or, for example, for a type of polarised wave.

An illumination function is described by a two-dimensional, complex-valued stationary wavefield $P_{actual}(x,y)$, which impinges upon the front surface of the object 310, i.e. the surface facing towards the source of illumination. In the following description P(x,y) represents an estimate of the illumination function, it being understood that reconstruction methods according to embodiments of the invention are designed to iterate upon an accurate estimate of: $P(x,y) \approx P_{actual}(x,y)$.

An intensity of a plurality J of diffraction patterns are recorded by a detector 320, wherein each diffraction pattern is indicated by j=1, 2 . . . J, which we denote as $I^j(u,v)$, where each of the J diffraction patterns is collected when the probe is at a corresponding position $P_{actual}(x-X_j, y-Y_j)$, where $X_j$ and $Y_j$ are displacements of the probe relative to the object 310 in the x,y plane. It is desirable that these displacements of the probe are arranged so that the area of the object 30 illuminated when the probe is at one position is partly the same as when the probe was at an adjacent position i.e. that the probe positions at least partly overlap, as is usual in two-dimensional implementations of PIE. It should also be understood that diffraction pattern data can also be collected with the illumination or object 310 shifted along the z direction, with data so-collected being used for a second or further repetition of the embodiments of the methods outlined below in order to refine the transmission function estimate $O_n(x,y)$. In some embodiments, further such data sets of diffraction pattern measurements may be collected with the object 310 having been rotated or tilted to a different orientation, as will be explained.

Some embodiments of the invention utilise four levels of iteration loops. A lowest (innermost') loop examines data collected from a single $j^{th}$ probe position, updating estimates of P(x,y) and $O_n(x,y)$ according to a 'forward' calculation and an inverse 'backward' calculation, variants of which will be described below. Outside this innermost loop, the method cycles over j, repeating the innermost loop for each of the J probe positions; this may be known as a 'field-of-view' loop. Outside the field-of-view loop, the whole field-of-view loop is repeated a number of times; this may be known as a 'single-orientation loop'. The field-of-view and the single-orientation loops are identical to the previously described PIE and ePIE methods. Previous applications by the present Applicant discuss how to improve the performance of such methods, such as by altering the order in which data from the J positions is arranged in the field-of-view loop, or by optimising the chosen displacements $X_j$ and $Y_j$ to minimise reconstruction artefacts. Such methods may be incorporated into embodiments of the present invention. Finally, an outermost loop may optionally repeat the lower-level loops using data collected from the object 30 after it has been tilted or rotated to one or more new orientations, as described below.

Embodiments of the present invention update the N running estimates of the transmission functions $O_n(x,y)$ whilst also maintaining a record of and/or updating running estimates of wave functions incident upon and exiting each transmission function $O_n(x,y)$ for both the forward calculation and the backward calculation.

The forward calculation models the modulus and phase of the scattered radiation, $\Psi_f(u,v)$, that would be expected to arrive in the diffraction pattern given the current estimate of P(x,y), the current estimates of each $O_n(x,y)$, for all $z_n$, the known position of the probe $X_j$ and $Y_j$, and the form of the propagator which propagates the exit wave emanating from the object 310 to the detector 320, which we call ℑ and which may be of the form of a Fresnel propagator, a Fraunhofer propagator, or other propagator.

An intensity constraint is employed in the diffraction plane: wherein the modulus of $\Psi_f(u,v)$ is replaced with $\sqrt{I_j(u,v)}$, but its phase is preserved to give $\Psi_b(u,v)$, as described in the PIE or ePIE references.

The backward calculation uses $\Psi_b(u,v)$ to reverse the scattering process, back-propagating radiation to the object 310 and updating the estimates of the transmission functions $O_n(x,y)$.

Each slice 340, 350 of the object 310 has associated with it a two-dimensional complex-valued wave function $\Psi_{f,n}^i(x,y)$ which is incident upon the front surface (facing the source of radiation) of the slice 340, 350. Each slice also has an associated wave function downstream of the respective slice, an exit wave, which has been modified by the properties of the slice $\Psi_{f,n}^e(x,y)$. In this nomenclature, superscripts i and e label incident and exit waves respectively. Subscript f indicates the estimate is derived from the forward calculation, and n indicates that this incident or exit wave relates to the $n^{th}$ slice. Similarly, $\Psi_{b,n}^i(x,y)$ and $\Psi_{b,n}^e(x,y)$ describe estimated wave functions incident upon and exiting the $n^{th}$ slice which have been computed during the backward calculation.

A wave propagator $\wp_{\Delta z}$ and its inverse $\wp_{\Delta z}^{-1}$, of the form of Fresnel or angular spectrum, or similar propagators, are used to propagate various ψ(x,y) forwards and backwards through distances Δz within the volume of the object 30. An object slice update operator is defined in Equation 2 as:

$$O_n^{next}(x,y) = \quad\quad\quad\quad\quad\quad\quad\quad\quad\quad \text{Equation 2}$$

$$O_n(x,y) + \alpha \frac{(\psi_{f,n}^i(x,y))^*}{|\psi_{f,n}^i(x,y)|_{max}^2}(\psi_{b,n}^e(x,y) - \psi_{f,n}^e(x,y))$$

where α is a constant between 0 and 2, which determines the speed of convergence of the algorithm, and * indicates the complex conjugate. Equation 2 may be written in a compact form $O_n(x,y) = U_o[O_n(x,y)]$ it being understood that the updated estimate $O_n^{next}(x,y)$ now becomes the current estimate of $O_n(x,y)$ i.e. $O_n(x,y) = O_n^{next}(x,y)$.

An illumination update function is defined in Equation 3 as $$\psi_{b,n}^i(x,y) = \psi_{f,n}^i(x,y) + \alpha \frac{(O_n(x,y))^*}{|O_n(x,y)|_{max}^2}(\psi_{b,n}^e(x,y) - \psi_{f,n}^e(x,y)) \quad \text{Equation 3}$$

which may similarly be written as $\psi_{b,n}^i(x,y) = U_{illum}[\psi_{f,n}^i(x,y)]$.

The method 200 will now be explained in more detail with reference to FIGS. 2 and 3. The method is particularly suitable if the object 30 is weakly scattering, although embodiments of the invention are not limited in this respect. The method 200 proceeds as follows:

In step 205 a first or initial probe position is selected in step 205. The first probe position need not be j=1, but may be another of the J probe positions, possibly selected at random.

In step 210 a current free-space estimate of the shifted probe is propagated to all planes at $z_n$ as:

$$\Psi_{f,n}^i(x,y) = \wp_{\Delta z_n}[P(x-X_j, y-Y_j)]$$

Figure 3:
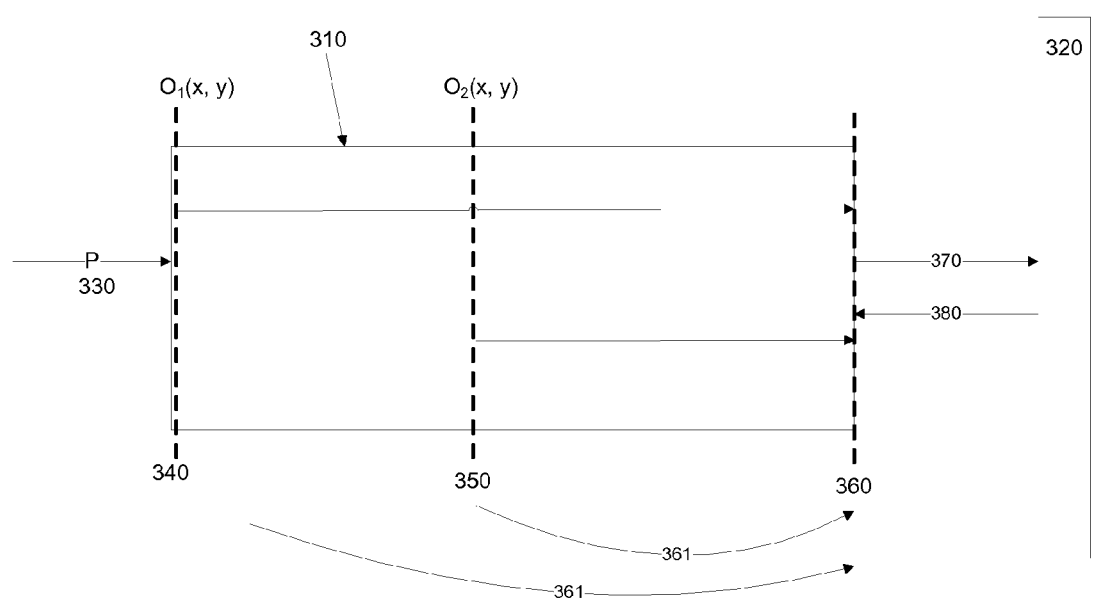
FIG. 3 shows an apparatus associated with the method of FIG. 2 according to an embodiment of the invention.

If $P(x-X_j, y-Y_j)$ is defined as lying at $z_0=0$, as in FIG. 3, which is itself coincident with the first slice 340 of the object 310, then $\Delta z_1=0$ and $\Delta z_2=z_2$, $\Delta z_3=z_3$, and so on. This process using two such slices 340, 350 is shown in FIG. 3.

In step 215 at each slice an exit wave is determined as: $\psi_{f,n}^e(x,y) = \psi_{f,n}^i(x,y) \cdot O_n(x,y)$.

In step 220 each such exit wave is then propagated to a summation plane 360 downstream of the object 310, which may also be the exit surface of the object 310, i.e. a downstream face of the object 310, as indicated by arrows 361.

In step 225 all the waves propagated to the summation plane 360 are added together. The summation at the summation plane 360 may be defined as:

$$\psi_{f,s}(x,y) = \wp_{z_s-z_1}[\psi_{f,1}^e(x,y)] + \wp_{z_s-z_2}[\psi_{f,2}^e(x,y)] + \wp_{z_s-z_3}[\psi_{f,3}^e(x,y)] + \ldots + \wp_{z_s-z_N}[\psi_{f,N}^e(x,y)].$$

In step 230 the summed exit wave $\psi_{f,s}(x,y)$ is propagated 370 to the detector 320, to give $\Psi_f(u,v) = \Im[\psi_{f,s}(x,y)]$, where its phase is retained but its modulus is set to $\sqrt{I_f(u,v)}$ to give $\Psi_b(u,v)$ in step 235.

In step 240 $\Psi_b(u,v)$ is back-propagated 380 to the summation plane 360, giving a different estimate of the wave (the 'backward calculated' wave) at the summation plane 360 $\psi_{b,s}(x,y) = \Im^{-1}[\Psi_b(u,v)]$.

In step 246, a slice of the reconstruction $O_n(x,y)$ is selected. The slice may be selected as the last slice 350 of the object i.e. immediately prior to the summation plane 360. However, other slices may also be selected, as discussed below.

In step 247, the propagated exit waves of all the other slices (except the selected slice n) calculated in the forward direction, are subtracted from the back propagated summation plane $\psi_{b,s}(x,y)$ to give $\psi_{b,s_n}(x,y)$. So for example, if the slice selected at step 246 is $O_1(x,y)$, then at step 247 we calculate:

$$\psi_{b,s_1}(x,y) = \psi_{b,s}(x,y) - \wp_{z_s-z_2}[\psi_{f,2}^e(x,y)] - \wp_{z_s-z_3}[\psi_{f,3}^e(x,y)] \ldots - \wp_{z_s-z_N}[\psi_{f,N}^e(x,y)].$$

Similarly, if the slice selected in step 246 is $O_2(x,y)$, then at step 247 we calculate:

$$\psi_{b,s_2}(x,y) = \psi_{b,s}(x,y) - \wp_{z_s-z_1}[\psi_{f,1}^e(x,y)] - \wp_{z_s-z_3}[\psi_{f,3}^e(x,y)] \ldots - \wp_{z_s-z_N}[\psi_{f,N}^e(x,y)].$$

At step 248 the remaining exit wave i.e. after the subtraction $\psi_{b,s_n}(x,y)$ is back propagated to the selected $n^{th}$ slice, and so on. So for example, if $O_2(x,y)$ is selected at step 246, it is back propagated to give:

$$\psi_{b,2}^e(x,y) = \wp_{z_s-z_1}^{-1}[\psi_{b,s_2}(x,y)],$$

and in general:

$$\psi_{b,n}^e(x,y) = \wp_{z_s-z_1}^{-1}[\psi_{b,s_n}(x,y)].$$

In step 249, for the selected slice to which the exit wave has been back propagated, an update of the object transmission function $O_n(x,y)$ is undertaken, to give $O_n(x,y) = U_o[O_n(x,y)]$. So for example, at the first slice 340 the associated transmission function is updated:

$$O_1^{next}(x,y) = O_1(x,y) + \alpha \frac{(\psi_{f,1}^i(x,y))^*}{|\psi_{f,1}^i(x,y)|_{max}^2}(\psi_{b,1}^e(x,y) - \psi_{f,1}^e(x,y)),$$

after which the assignment $O_1(x,y) = O_1^{next}(x,y)$ is made so that the updated transmission function now becomes the current estimate of the transmission function.

In step 250 it is determined whether all slices have been considered i.e. the transmission function associated with each slice has been updated. If all slices have not yet been considered, the method returns to step 246 and steps 246-249 are repeated for the next selected slice until all slices have been considered.

In step 255 a current estimate of the probe function $P(x-X_j, y-Y_j)$ is updated at one of the slices 340, 350, or at the summation plane 360. The probe function may be updated at the first slice 340, for example, as follows:

$$P(x-X_j, y-Y_j) = \psi_{f,1}^i(x,y) + \alpha \frac{(O_1(x,y))^*}{|O_1(x,y)|_{max}^2}(\psi_{b,1}^e(x,y) - \psi_{f,1}^e(x,y)),$$

If the probe update is undertaken at another plane, then it is the propagated estimate of the incident probe used in the forward calculation that is updated. For a probe propagating in free space (as in this embodiment of the invention) defining the probe at any one slice defines it for all others, including at the entrance plane and summation plane.

The innermost loop formed by steps 210-255 may be repeated from step 210, although in general it is preferable now to select a new probe position j in steps 260-265, by determining whether all of the J probe positions have been considered, and thus continue with the field-of-view iteration, passing through steps 210-255 for all subsequent probe positions, employing the respective diffraction pattern data for each position.

When all J probe positions have been addressed in the field-of-view loop, further field-of-view loops may be undertaken until a condition is met or a certain number of field-of-view iterations have been performed, as determined in step 270. If a further iteration of the outermost loop is to be performed, the probe position may be reset in step 275, for example to the initial probe position utilised in step 205.

A second embodiment of the invention will now be described which is particularly suited to situations where the object 30 is strongly scattering, although embodiments of the invention are not limited in this respect. 'Strongly scattering' means that the first Born approximation is not satisfied. In other words, the illumination at a point within the object 30 has been substantially affected by scattering that has occurred within layers of the specimen upstream of that point. The second embodiment of the invention differs from the first embodiment in the steps undertaken in the innermost loop of the algorithm.

In the second embodiment of the invention, scattering in the forward propagation is performed by using the propagated exit wave from one slice to act as the incident wave on the next slice, while the backward calculation reverses this procedure, updating both the probe function and the transmission function at each slice, and then back propagating the updated probe function to the previous slice, and so on and so forth, until finally a new estimate of the incident illumination function is obtained. The second embodiment may be described as follows with reference to FIGS. 4 and 5 with reference to an example including an object 510, incident radiation 530, a detector 520 and two slices 540, 550, although it will be realised that further slices may be considered.

As in the embodiment previously described with reference to FIG. 2, in step 405 an initial probe position is selected, as in step 205 of the previously described method. In step 405 a first plane 540 of an object 510 is also selected which is the front-most i.e. toward the radiation source 530.

In step 410, an incident wave 530 upon the current slice of the object is determined as $\psi_{f,n}^i(x,y) = P(x-X_j, y-Y_j)$, which for the first iteration of step 410 is the current estimate of the illuminating wave incident upon the first slice 540 of the object for the probe at the $j^{th}$ position, for which diffraction data $I_i(u,v)$ has been recorded or measured.

In step 415 an exit wave from the current slice, $\psi_{f,n}^e(x,y) = \psi_{f,n}^i(x,y) \cdot O_1(x,y)$ is determined.

If, in step 420 the current slice is not the last slice of the object, then the method moves to step 425. In other words, if a subsequent slice of the object exists, the method moves to step 425. The subsequent slice 550 may be the next, adjacent, slice in a downstream direction. In the first iteration of step 420, for the example of FIG. 5, the subsequent slice is the second slice 550.

In step 425, the exit wave from the slice 540 is propagated to the subsequent slice 550, creating a subsequent incident wave $\psi_{f,n+1}^i(x,y) = \wp_{\Delta z_1}[\psi_{f,n}^e(x,y)]$, where $\Delta z_1 = z_2 - z_1$.

Returning to step 415, an exit wave from the next slice 550 is determined $\psi_{f,n+1}^e(x,y) = \psi_{f,n+1}^i(x,y) \cdot O_{n+1}(x,y)$.

If, in step 420, there exists a further, subsequent slice, the exit wave is propagated to the next slice, creating a subsequent incident wave $\psi_{f,n+2}^i(x,y) = \wp_{\Delta z_2}[\psi_{f,n+1}^e(x,y)]$, where $\Delta z_{n+1} = z_{n+2} - z_{n+1}$. This process is repeated similarly for each successive slice 540, 550 of the object 510, until we obtain an estimate of the final exit wave, $\psi_{f,N}^e(x,y)$. The estimate of the final exit wave for FIG. 5 is that exiting from slice 550, wherein in step 420 the slice 550 is determined to be the final slice of the object and the method moves to step 430.

In step 430 the final exit wave $\psi_{f,N}^e(x,y)$ is propagated to the detector 40, giving $\Psi_f(u,v) = \Im[\psi_{f,N}^e(x,y)]$, where its phase is retained but its modulus is set to $\sqrt{I_i(u,v)}$ to give $\Psi_b(u,v)$ i.e. the intensity constraint is applied in step 435.

In step 440 the updated wave at the detector $\Psi_b(u,v)$ is back-propagated to the exit slice i.e. the final slice 550 in the example of FIG. 5, giving $\psi_{b,N}^e(x,y) = \Im^{-1}[\Psi_b(u,v)]$.

In step 445, the transmission function and probe function at the slice are updated. The transmission function and illumination function may be updated as described in the ePIE reference according to the following:

$$O_n^{next}(x,y) = O_n(x,y) + \alpha \frac{(\psi_{f,n}^i(x,y))^*}{|\psi_{f,n}^i(x,y)|_{max}^2}(\psi_{b,n}^e(x,y) - \psi_{f,n}^e(x,y))$$

Similarly, an illumination function update such as that described in the ePIE reference may also undertaken to compute a new backward estimation of the wave that is incident upon that slice, namely:

$$\psi_{b,n}^i(x,y) = \psi_{f,n}^i(x,y) + \alpha \frac{(O_n(x,y))^*}{|O_n(x,y)|_{max}^2}(\psi_{b,n}^e(x,y) - \psi_{f,n}^e(x,y)).$$

In step 450, it is determined whether the current slice is the first i.e. a front-most slice of the object. If the current slice is not the first slice, the method moves to step 455.

In step 455, the updated estimate of the wave function at the current slice is back-propagated to previous slice according to $$\psi_{b,n-1}^e(x,y) = \wp_{\Delta z_{n-1}}^{-1}[\psi_{b,n}^i(x,y)],$$

where $\Delta z_{n-1}$ is the distance between slice n and the previous slice n-1.

In step 445, updates occur on both the associated transmission function, $O_{n-1}(x,y) = U_o[O_{n-1}(x,y)]$ and the illumination function incident on that slice $\psi_{b,n-1}^i(x,y) = U_{illum}[\psi_{f,n-1}^i(x,y)]$ as in the previous iteration of step 445.

In step 450, if there remain further previous slices, the newly-estimated function $\psi_{b,n-1}^i(x,y)$ is back propagated to the next previous slice, where a further pair of updates are undertaken, and so on and so forth through all slices 540, 550, employing the generalised updates functions in Equations 2 and 3, until eventually a new estimate of the illumination on the front surface of the object 510, $P(x-X_j, y-Yj) = \psi_{b,1}^i(x,y)$ is determined.

The innermost iteration for the second embodiment can be repeated from step 405, although in general it is preferable now to select a new probe position j, if all the probe positions have not been considered, as in step 460. The new probe position is selected in step 465. The updated estimate of illumination at the first plane $P(x,y)$ calculated in step 445 is used as the illumination at the first plane in step 410, which is re-selected in step 470 as the current plane. Steps 410-455 are repeated for all subsequent probe positions, employing the respective diffraction pattern data for each position.

In step 460, if all probe positions have been addressed in the field-of-view iteration, the method moves to step 475 where further field-of-view iterations are undertaken until a condition is met, or a certain number of field-of-view iterations have been finished, as discussed in the cited references. If the method is repeated, the probe position is reset and the first plane re-selected in step 480.

As introduced above, embodiments of the present invention may be utilised to determine transmission functions for a plurality of slices intersecting an object, wherein each of the plurality of slices is angled to a respective angle. That is, at least some of a plurality of slices intersect each other and are angled to a respective angle, as will be explained.

Figure 4:
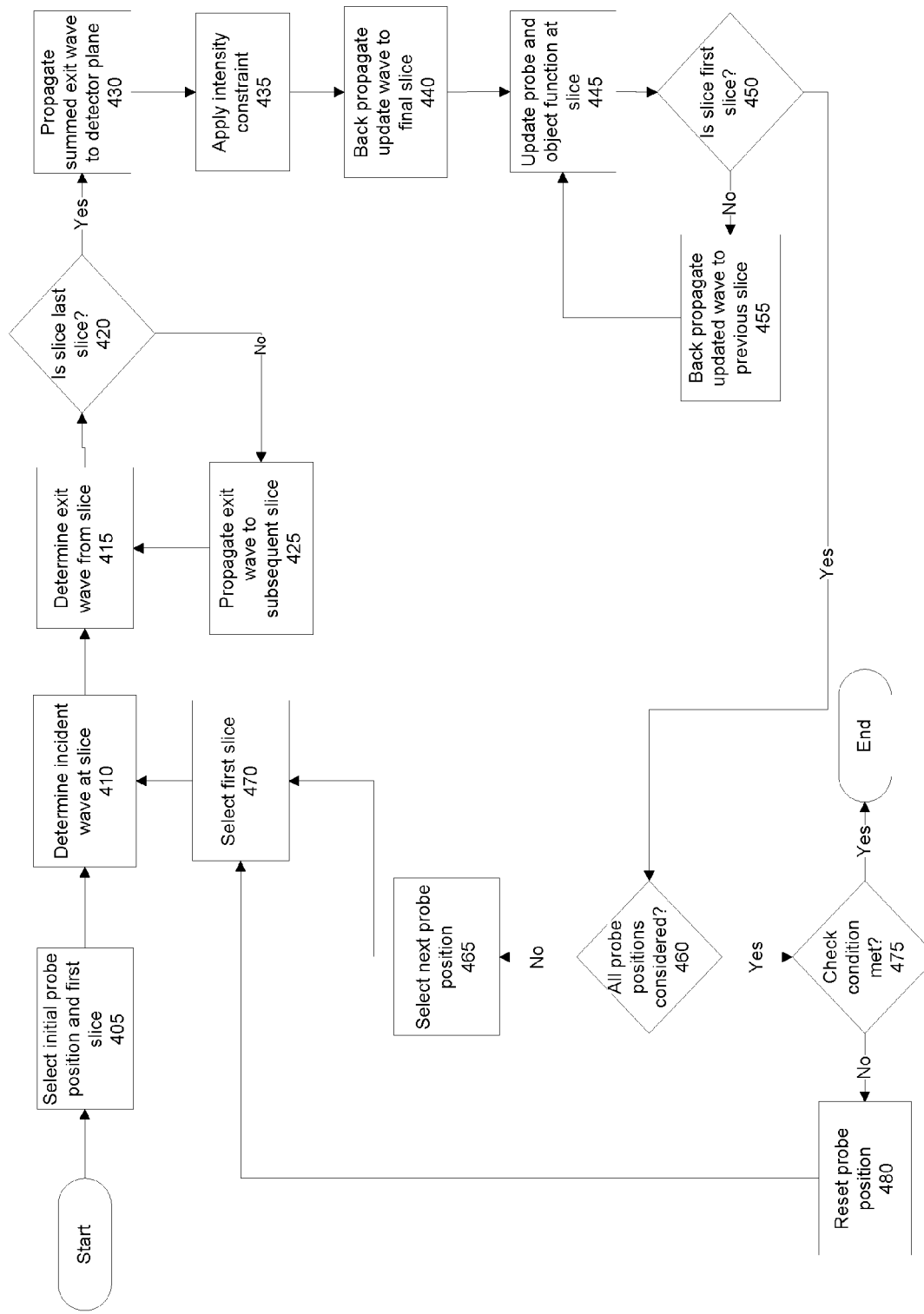
FIG. 4 shows a second method according to an embodiment of the invention.

Embodiments of the invention determine transmission functions at a plurality of slices spaced apart along the optic axis, for example as shown in FIG. 1. The transmission function associated with each slice may be determined by any of the methods described above. Although the object 30 may initially be arranged at any orientation with respect to the optic axis, i.e. the initial physical orientation of the object may be chosen as desired, an initial orientation of the slices shown in FIG. 1 will be referred to as 0° with respect to the object 30. By utilising either of the methods described above, i.e. as shown in FIG. 2 or 4, a respective transmission function may be determined associated each slice 31, 32.

FIG. 6 illustrates the apparatus as shown in FIG. 1 according to an embodiment of the invention with first and second slices 31, 32 intersecting the object 30, but with the object 30 rotated to a first angle in FIG. 6(a) and a second angle in FIG. 6(b). Embodiments of the invention may then be used to determine one or further transmission functions associated with each slice, each associated with a respective rotation of the object 30.

In a first step, an embodiment of the present invention is utilised to determine transmission functions associated with slices 31, 32 at 0° with respect to the object 30. Referring to FIG. 1 two transmission functions are determined associated with slice 31, 32 at 0°. Following the determination of a first plurality of transmission functions, the object 30 is rotated to another angle, as shown in FIG. 6(a). The position of the object 30 remains constant with respect to the optic axis 50. An embodiment of the invention, preferably the same embodiment previously used, is then arranged to perform a second iteration to determine a second plurality of transmission functions at each of the slices 31, 32 but with the object 30 at an angle, such as 15°.

Figure 8:
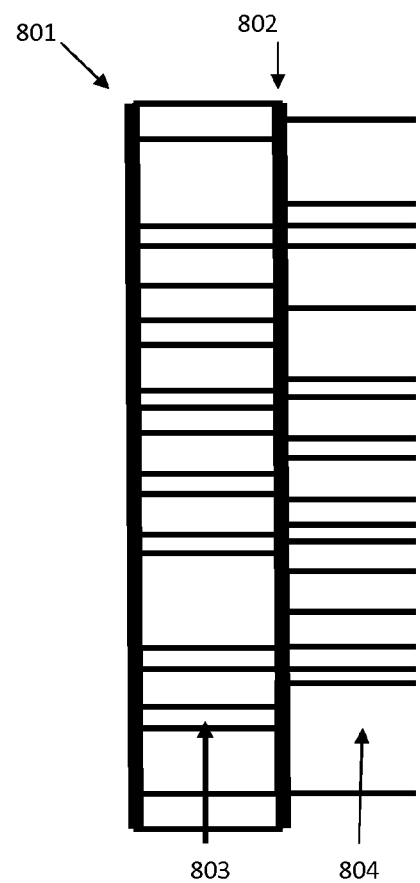
FIG. 8 illustrates determining image data for an object at a plurality of orientations according to an embodiment of the invention.
Figure 9:
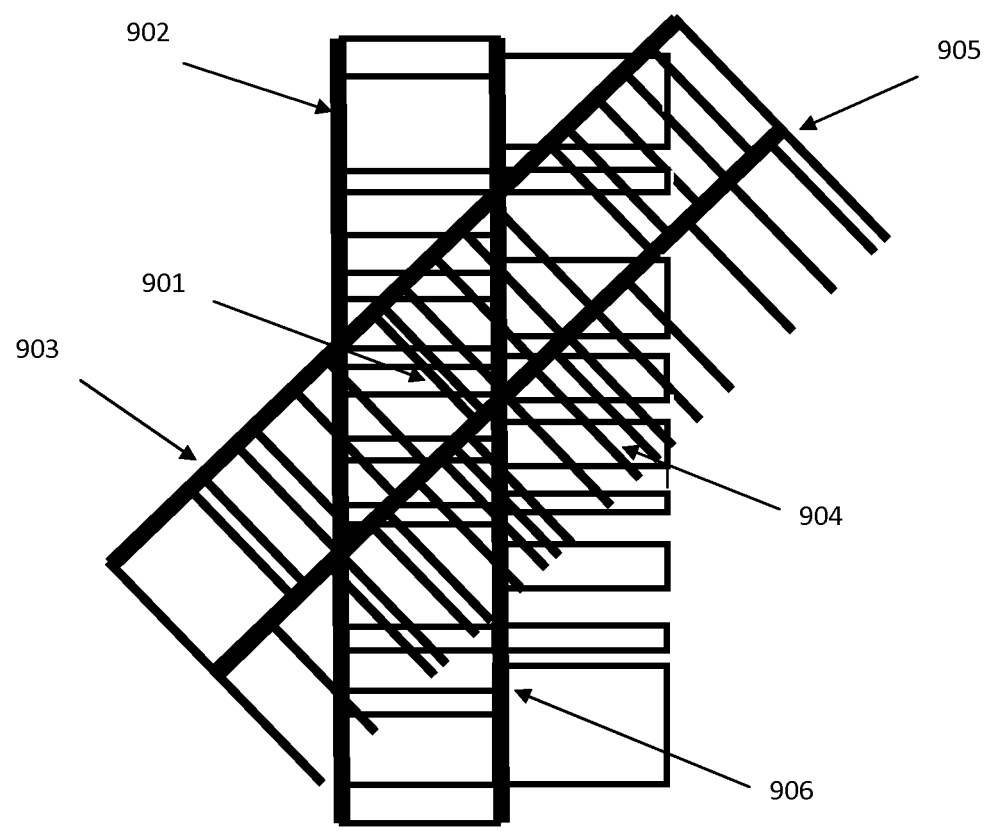
FIG. 9 further illustrates determining image data for an object at a plurality of orientations according to an embodiment of the invention.

By inverting Equation 1, and with reference to FIG. 8, two or more two-dimensional transmission functions, 801 and 802, are derived according to the present invention, to back project optical potentials 803 and 804 respectively through fractional depths of the object 30. In FIG. 9, multiple two-dimensional transmission functions collected with the object 30 at different orientations, as according to the present invention, can be used to construct back projections over various volumes of the object 30. For example, the volume 901 comprises two back projections derived from the slices 902 and 903; the volume 904 comprises two back projections derived from the slices 905 and 906 and so on. By adding filtered back-projections over voxels occupying the entire volume of the object 30, an estimate of the three-dimensional object is obtained. A filtered back-projection will be understood by those familiar with the art to relate to a method of conventional tomography where only one back projection is available through the entire volume of the object, whereas here multiple volumes such as 901 and 904 are processed. The data can be collected from many object orientations before the reconstruction process is undertaken, and the order in which data from different orientations is processed may be chosen at will.

In some embodiments, an input to the second iteration is the transmission function derived from the back projected potential from the first iteration. For example, for slice 31, the transmission function derived from Equation 1 using the back projected transmission function determined at 0° is used as a first transmission function for that slice 31, which intersects the slice in the second iteration with the object at a different angle. Advantageously, this allows faster determination of the transmission function in the second iteration. Following determination of the second plurality of transmission functions at the second object rotation angle, further iterations of the method may be performed at respective angular rotations of the object 30, as shown in FIG. 6(b) to determine a third, or further, plurality of transmission functions each associated with one of the slices 31, 32. Furthermore, each update iteration for data from each orientation may be interleaved with update iterations using data from other orientations.

Unlike existing tomographic techniques, the present invention advantageously takes into account the effects of the coherent three-dimensional scattering integral, the evolution of the illuminating beam as it propagates through the object, and multiple scattering effects. Those skilled in the art will understand that the number of object tilts required for an accurate conventional filtered back-projection tomographic reconstruction increases in proportion with the object thickness. Since in the present invention the object is decomposed into slices which are a fractional thickness of the object, the number of such tilts required for an accurate tomographic reconstruction of the object is advantageously smaller than for current state-of-the-art techniques.

Figure 7:
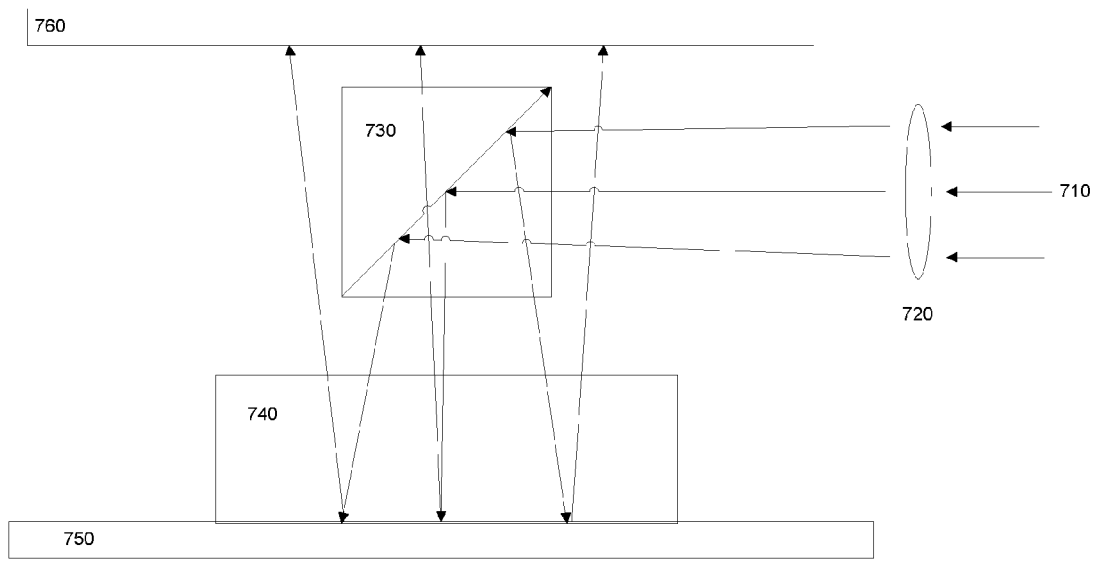
FIG. 7 shows an apparatus according to a further embodiment of the invention.

Embodiments of the present invention may also be used with at least partially transparent objects. FIG. 7 illustrates an apparatus according to an embodiment of the invention for use with at least partially transparent objects to determine object functions associated with the object.

Incident radiation 710 is directed toward a focussing arrangement 720, such as a lens, as previously described, which focuses the radiation toward a beam splitter 730. The beam splitter is arranged to direct incident radiation from the lens 720 toward an object 740 by redirecting the incident radiation by 90° toward the object 740. Radiation subsequently penetrates the at least partially transparent object before encountering a mirrored surface 750 at a downstream side of the object 740. For example, the object 740 may be placed upon the mirrored surface 750. Radiation is reflected by the mirrored surface 750 back toward the beam splitter. Reflected radiation may not necessarily encounter the beam splitter i.e. it may be reflected at an angle such that it passes the beam splitter 730. However, the beam splitter is arranged to not direct reflected radiation, as is known in the art. Reflected radiation passes through the beam splitter to be measured by a detector 760. In some embodiments, the reflective surface 750 may be arranged below the object 740 with the detector 760 arranged above the object 740 and beam splitter 730. This configuration is optically equivalent to the transmission case previously described, but this time with the specimen appearing twice, one version reflected in the z-direction, which is downstream of the first version.

It will be appreciated that embodiments of the present invention can be realised in the form of hardware, software or a combination of hardware and software. Any such software may be stored in the form of volatile or non-volatile storage such as, for example, a storage device like a ROM, whether erasable or rewritable or not, or in the form of memory such as, for example, RAM, memory chips, device or integrated circuits or on an optically or magnetically readable medium such as, for example, a CD, DVD, magnetic disk or magnetic tape. It will be appreciated that the storage devices and storage media are embodiments of machine-readable storage that are suitable for storing a program or programs that, when executed, implement embodiments of the present invention. Accordingly, embodiments provide a program comprising code for implementing a system or method as claimed in any preceding claim and a machine readable storage storing such a program. Still further, embodiments of the present invention may be conveyed electronically via any medium such as a communication signal carried over a wired or wireless connection and embodiments suitably encompass the same.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings), may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed. The claims should not be construed to cover merely the foregoing embodiments, but also any embodiments which fall within the scope of the claims.

The invention claimed is:

1. A method of providing image data for constructing an image of a region of a three dimensional target object, comprising:
   providing, from a radiation source, incident radiation directed at a target object;
   detecting an intensity of radiation scattered by the target object;
   for each iteration of an iterative process, determining image data for each of a respective plurality of slices within the target object each indicating one or more characteristics of the target object at a respective depth within the target object, wherein the image data for each of the plurality of slices is determined based on the detected intensity of radiation wherein running estimates of the image data for each of the plurality of slices are updated step by step with each iteration of said iterative process.

2. The method of claim 1, wherein the image data for each slice is determined based upon an integral of a property of the object between first and second surfaces.

3. The method of claim 2, wherein the property of the object is one of: an optical potential or an atomic potential of the object.

4. The method of claim 3, further comprising determining a running estimate of a transmission function for each slice indicating at least one characteristic of the target object.

5. The method of claim 4, wherein the transmission function is based upon the integral of the property of the object between the surfaces.

6. The method of claim 4, wherein an accuracy of the running estimates of the transmission functions is improved by re-estimating the transmission functions with each step.

7. The method of claim 1, further comprising providing said image data responsive to at least the detected intensity of the radiation at first and second positions with respect to the target object.

8. The method of claim 7, wherein the first and second positions are formed using a softly varying transmittance function, or illumination function, movable with respect to said target object.

9. The method of claim 1, further comprising:
   determining a probe function indicative of one or more characteristics of the incident radiation incident on each of the plurality of slices;
   determining an exit wave estimate for each of the slices based on the probe function and a transmission function associated with each respective slice;
   determining a combined exit wave estimate by propagating each exit wave to a surface and combining each of the exit waves at that surface.

10. The method of claim 9, wherein the probe function indicates an estimate of the incident radiation propagating in free space corresponding to a depth of each slice.

11. The method of claim 9, further comprising propagating the combined exit wave from the surface to the detector to determine an expected scattering pattern at the detector.

12. The method of claim 11, further comprising correcting at least one characteristic of said expected scattering pattern according to the detected intensity.

13. The method of claim 12, further comprising inversely propagating the corrected expected scattering pattern to provide an updated estimate of the combined exit wave at the surface.

14. The method of claim 13, further comprising determining a portion of the updated estimate of the combined exit wave corresponding to each slice and inversely propagating the respective portion to each slice.

15. The method of claim 14, further comprising updating the transmission function associated with each respective slice based upon the inversely propagated respective portion.

16. The method of claim 15, wherein the exit waves are combined at the surface by summation of the exit waves.

17. The method of claim 15, wherein the portion of the combined exit wave corresponding to each slice is determined by subtracting the exit waves propagated to the surface from other slices.

18. The method of claim 17, further comprising updating the probe function at one of the slices based upon the inversely propagated respective portion of the updated estimate of the combined exit wave.

19. The method of claim 1, further comprising:
   determining a probe function indicative of one or more characteristics of the incident radiation upon a first slice;
   determining a first exit wave estimate for the first slice based on the probe function and a transmission function associated with the first slice;
   propagating the first exit wave to a second slice, wherein the propagated first exit wave forms a probe function for the second slice; and
   determining a second exit wave estimate for the second slice based on the probe function and a transmission function associated with the second slice.

20. The method of claim 19, comprising determining probe functions and exit wave estimates for one or more further slices of the object.

21. The method of claim 20, comprising propagating an exit wave from a final slice of the object to the detector to determine an expected scattering pattern at the detector.

22. The method of claim 21, comprising correcting at least one characteristic of said expected scattering pattern according to the detected intensity.

23. The method of claim 22, comprising inversely propagating the corrected expected scattering pattern to provide an updated estimate of the exit wave from the final slice.

24. The method of claim 23, comprising updating the transmission function associated with the final slice based upon the updated estimate of the exit wave.

25. The method of claim 24, comprising updating the probe function incident on the final slice based upon the updated estimate of the exit wave.

26. The method of claim 25, comprising inversely propagating the updated probe function to a previous slice as the updated exit wave for that slice.

27. An apparatus for providing image data for generating an image of at least one region of a target object, comprising:
- a radiation source for providing incident radiation at a target object;
- at least one detector device for detecting an intensity of radiation scattered by said target object;
- a processor that provides the image data responsive to a detected intensity of the scattered radiation, wherein the said processor is configured to provide image data for each of a respective plurality of slices within the target object each indicating one or more characteristics of the target object at a respective depth within the target object, wherein the processor is configured to, for each iteration of an iterative process, determine the image data for each of the plurality of slices based on the detected intensity of the radiation wherein running estimates of the image data for each of the plurality of slices are updated step by step with each iteration of said iterative process.

28. The apparatus of claim 27, wherein the processor is arranged to determine image data for each slice based upon an integral of a property of the object between first and second surfaces.

29. A non-transitory computer readable medium storing instructions for providing image data for constructing an image of a region of a three dimensional target object, the instructions being executable by at least one processor of a computer system, the instructions instructing the computer system to determine for each iteration of an iterative process from an intensity of radiation scattered by the target object image data for each of a respective plurality of slices within the target object, each image data indicating one or more characteristics of the target object at a respective depth within the target object, wherein the image data is determined for each of the plurality of slices based on the detected intensity of radiation, wherein running estimates of the image data for each of the plurality of slices are updated step by step of said iterative process.

* * * * *